US008817262B2

(12) United States Patent  
Bogdanowicz (10) Patent No.: US 8,817,262 B2  
(45) Date of Patent: Aug. 26, 2014

(54) METHOD FOR DETERMINING THE DOPING PROFILE OF A PARTIALLY ACTIVATED DOPED SEMICONDUCTOR REGION

(71) Applicants: IMEC, Leuven (BE); Katholieke Universiteit Leuven, Leuven (BE)

(72) Inventor: Janusz Bogdanowicz, Liege (BE)

(73) Assignees: IMEC, Leuven (BE); Katholieke Universiteit Leuven, Leuven (BE)

( * ) Notice: Subject to any disclaimer, the term of this patent is extended or adjusted under 35 U.S.C. 154(b) by 0 days.

(21) Appl. No.: 13/689,540

(22) Filed: Nov. 29, 2012

(65) Prior Publication Data

US 2013/0335744 A1 Dec. 19, 2013

Related U.S. Application Data

(63) Continuation of application No. 12/492,062, filed on Jun. 25, 2009, now abandoned.

(60) Provisional application No. 61/076,559, filed on Jun. 27, 2008.

(51) Int. Cl.
 *G01N 21/55* (2014.01)
 *H01L 21/66* (2006.01)
 *G01N 21/17* (2006.01)

(52) U.S. Cl.
 CPC ............... *G01N 21/55* (2013.01); *H01L 22/12* (2013.01); *G01N 2021/1725* (2013.01); *G01N 2021/1731* (2013.01); *G01N 21/1717* (2013.01); *G01N 2021/1719* (2013.01)
 USPC .......................... 356/445; 356/237.1; 250/372

(58) Field of Classification Search
 USPC ......... 356/432, 445, 447, 502, 237.1; 438/16; 250/372
 See application file for complete search history.

(56) References Cited

U.S. PATENT DOCUMENTS 6,812,047 B1 11/2004 Borden et al.  
6,917,039 B2 7/2005 Nicolaides et al.  
(Continued)

FOREIGN PATENT DOCUMENTS

WO WO 2007/028605 3/2007

OTHER PUBLICATIONS

Bogdanowicz et al., Impact of inactive dopants in chemical vapor deposition layers on photomodulated optical reflectance, Materials Science and Engineering B, Elsevier Sequoia, Lausanne, CH, vol. 1544-155, Dec. 5, 2008, pp. 234-239.

(Continued)

*Primary Examiner* — Tarifur Chowdhury  
*Assistant Examiner* — Isiaka Akanbi  
(74) *Attorney, Agent, or Firm* — Knobbe, Martens, Olson & Bear LLP (57) ABSTRACT

A method is disclosed for determining the inactive doping concentration of a semiconductor region using a PMOR method. In one aspect, the method includes providing two semiconductor regions having substantially the same known as-implanted concentration but known varying junction depths. The method includes determining on one of these semiconductor regions the as-implanted concentration. The semiconductor regions are then partially activated. PMOR measures are then performed on the partially activated semiconductor regions to measure (a) the signed amplitude of the reflected probe signal as function of junction depth and (b) the DC probe reflectivity as function of junction depth. The method includes extracting from these measurements the active doping concentration and then calculating the inactive doping concentration using the determined total as-implanted concentration and active doping concentration. The method may also include extracting thermal diffusivity, refraction index, absorption coefficient, and/or SRHF lifetime from these measurements.

17 Claims, 5 Drawing Sheets

(56) References Cited

U.S. PATENT DOCUMENTS

| | | | |
|---|---|---|---|
| 6,940,592 B2 | 9/2005 | Borden et al. | |
| 7,130,055 B2 | 10/2006 | Borden et al. | |
| 7,465,591 B2 | 12/2008 | Borden et al. | |
| 7,522,287 B2 * | 4/2009 | Takahashi et al. | 356/503 |
| 7,660,686 B1 | 2/2010 | Nicolaides et al. | |
| 2003/0043382 A1 | 3/2003 | Borden et al. | |
| 2004/0196464 A1 | 10/2004 | Akutsu et al. | |
| 2004/0253751 A1 | 12/2004 | Salnik et al. | |
| 2005/0083528 A1 | 4/2005 | Salnik et al. | |
| 2005/0190369 A1 | 9/2005 | Salnik et al. | |
| 2005/0225765 A1 | 10/2005 | Nicolaides et al. | |
| 2008/0036998 A1 | 2/2008 | Salnik et al. | |

OTHER PUBLICATIONS

Extended European search report for European patent application No. 09163837.9, dated Mar. 5, 2012.

Bogdanowicz et al., Advances in optical carrier profiling through high-frequency modulated optical reflectance, Progress Journal of Vacuum Science & Technology B, Jan./Feb. 2008, No. 26, pp. 310-316.

Dortu et al., Progress in the physical modeling of carrier illumination, Journal of Vacuum Science & Technology B, May/Jun. 2006, No. 24, pp. 1131-1138.

Salnick et al., Quantitative photothermal characterization of ion-implanted layer in Si, Journal of Applied Physics, Mar. 1, 2002, vol. 91, No. 5, pp. 2874-2882.

Vitkin et al., Photothermal reflectance investigation of processed silicon. II. Signal generation and lattice temperature dependence in ion-implanted and amorphous thin layers, Journal of Applied Physics, Mar. 15, 1990, 67, pp. 2822-2830.

* cited by examiner

METHOD FOR DETERMINING THE DOPING PROFILE OF A PARTIALLY ACTIVATED DOPED SEMICONDUCTOR REGION

CROSS-REFERENCE TO RELATED APPLICATIONS

This application is a continuation of U.S. patent application Ser. No. 12/492,062, filed Jun. 25, 2009, titled "METHOD FOR DETERMINING THE DOPING PROFILE OF A PARTIALLY ACTIVATED DOPED SEMICONDUCTOR REGION", which application claims priority under 35 U.S.C. §119(e) to U.S. provisional patent application 61/076,559 filed on Jun. 27, 2008. Each of the above applications is hereby incorporated by reference in its entirety.

BACKGROUND OF THE INVENTION

1. Field of the Invention

This present disclosure relates to methods and/or procedures for determining in a non-destructive way the doping profile of a doped semiconductor region. Such a region can be a doped semiconductor layer formed on a high-resistivity substrate.

This present disclosure relates to methods and/or procedures for determining in a non-destructive way the physical properties of a semiconductor region.

2. Description of the Related Technology

The ITRS roadmap highlights the precise characterization of ultra-shallow junctions (USJs) as one of the top challenges for sub-32 nm Si-CMOS technologies. While the semiconductor technology size reaches the limits of the usually used physical and electrical analytical techniques (secondary ion mass spectrometry (SIMS), spreading resistance profiling (SRP), four-point probe (FPP)), alternative candidates, (e.g. scanning spreading resistance microscopy (SSRM)) are destructive and quite slow, e.g. as samples have to be prepared, and therefore prevent any in-line measurements.

Photomodulated optical reflectance (PMOR) is a widely used contactless technique where a modulated-power pump laser is directed towards a semiconductor sample to modify the refractive index profile thereof. This refractive index profile can be modified through generation of excess carriers, also known as the Drude effect, in the sample and/or by temperature effects of the sample under study. A probe laser is also directed to the semiconductor sample where it will be reflected depending on the refractive index profile. By coupling the reflected probe laser signal to a lock-in amplifier, only the variations in the reflectivity of the semiconductor sample induced by the modulated pump laser are measured.

An example of such PMOR technique is the Therma-Probe® technique (TP), which is a high-modulation-frequency implementation of the PMOR technique. In international patent application WO2007028605 titled "A method and device to quantify active carrier profiles in ultra-shallow semiconductor structures", the TP method is described. The measurement tool used consisted of two lasers, the pump laser and the probe laser, which are both normally incident on the surface of this semiconductor structure. The pump laser is operated at a wavelength $\lambda_{pump}$=790 nm, with pump power $P_{pump}$=13.5 mW and a laser radius $R_{pump}$=0.5 µm while being modulated at a 1 MHz modulation frequency. The probe laser is operated at a wavelength $\lambda_{probe}$=670 nm, while the power $P_{probe}$ is kept constant=2.5 mW and the laser $R_{probe}$=0.5 µm.

When incident on the substrate the pump laser generates different excess carrier concentration in the doped semiconductor structure and in the substrate. This difference in excess carrier concentration is due to the difference in recombination lifetime between this semiconductor region and the underlying substrate and to the electric field at the metallurgical junction between this semiconductor region and this substrate. By modulating the power of the pump laser with a modulation frequency ω=1 MHz, a modulated excess carrier profile is created with two steep changes, respectively at the surface of the doped semiconductor region and at this metallurgical junction.

This modulated excess carrier profile will result in a modulated refractive index profile with similar steep variations; the relationship between both profiles, i.e. refractive index and free carriers, can be derived using the known Drude model. Due to the interference between the surface and metallurgical junction reflection components of the incident probe laser, the modulated reflectance of the probe laser is representative of the semiconductor doping profile.

As the phase shift of the modulated reflectance with respect to the pump power signal also proved to be dependent on the semiconductor dopant profile, two independent signals can be obtained from the reflected probe laser signal. This is enough information to reconstruct a box-like active doping profile with two unknown parameters N (active doping concentration) and Xj (metallurgical junction depth). The generalization of this measurement procedure to more complex profiles uses either a varying maximum pump power (power curves) or a varying distance between the two lasers (offset curves) as to generate more independent signals. The temperature profile in the semiconductor region is linked via an empirical relationship with the refractive index profile.

Photomodulated optical reflectance (PMOR) technique such as the TP technique has shown its very promising electrical characterization capabilities on box-like doping profiles. TP has indeed proved to be able to characterize such box-like doping profiles in one single fast and non-destructive measurement. However, as the relationship linking PMOR signals to the measured doping profiles is not straightforward, the further use of TP for electrical characterization needs a critical modeling step. Yet, so far, the attempts to model quantitatively the PMOR signals on box-like doping profiles have encountered severe problems. In particular, these models fail when the total integrated concentration of the measured semiconductor structure increases, i.e. when either the junction depth or the total dose increases.

The PMOR methods, in particular the TP method, however only allow characterizing an active doping profile, i.e. providing only information of the spatial distribution of those dopant atoms that provided a free carrier. In case not all dopant atoms are activated, only the active component of the doping profile of semiconductor structure can be characterized. For high total integrated dose even this active doping profile can not be determined accurately using the PMOR method. Moreover the PMOR method doesn't take into account the influence of the inactive part of the doping profile on the physical characteristics, in particular the complex refractive index and the lifetime of the doped semiconductor structure. As these physical characteristics are influenced by the degree of activation of the semiconductors sample under study, the relationship between the measured reflected probe signal and the active dopant profile will also depend on the degree of activation.

SUMMARY OF CERTAIN INVENTIVE ASPECTS

A method is disclosed for determining the inactive doping concentration of a semiconductor region using a PMOR method, the method comprising: providing a set of at least two semiconductor regions having substantially the same known as-implanted concentration but known varying junction depth, determining on at least of these semiconductor regions the as-implanted concentration, partially activating at least two semiconductor regions from the semiconductor set, measuring by a Photomodulated Optical Reflectance (PMOR) technique on the partially activated semiconductor regions the signed amplitude of the reflected probe signal as function of junction depth and for at least two laser separation values, measuring by a Photomodulated Optical Reflectance (PMOR) technique on the partially activated semiconductor regions the DC probe reflectivity as function of junction depth, extracting from these measurements the active doping concentration thereby assuming crystal mobility, and, calculating the inactive doping concentration using the determined total as-implanted concentration and active doping concentration.

The method can further comprise the step of extracting thermal diffusivity, refraction index, absorption coefficient, and/or Shockley-Reed-Hall lifetime from these measurements.

The PMOR technique can be a high-modulation-frequency PMOR technique providing a signal in-phase with modulation signal and a signal with a 90° phase difference with respect to the probe laser beam.

The modulation frequency of the pump laser beam high-modulation-frequency PMOR technique can be in the Mhz range.

The integrated concentration of the doped semiconductor region is preferably about 1e20 cm$^{-3}$ or higher.

A method is disclosed for determining the effect and/or efficiency of annealing steps on physical properties of a doped semiconductor region the method comprising: (a) providing at least one sample of the doped semiconductor region, (b) determining the doping profile of the at least one sample, (c) applying an anneal step to the at least one sample, and (d) extracting the selected physical property by means any of the determination methods in the foregoing paragraphs to the annealed at least one sample.

This method can further comprise repeating steps (a) to (d) for another sample whereby another anneal step is applied, and correlating the variation in the physical property to the variation in anneal process.

The extracted physical property is selected from the group: thermal diffusivity, complex refraction index, absorption coefficient, and/or Shockley-Reed-Hall lifetime.

In one aspect, a method of determining the inactive doping concentration of a semiconductor region using a photomodulated optical reflectance (PMOR) method is disclosed. The method comprises providing a set of at least two semiconductor regions having substantially the same as-implanted concentration but different known junction depth. The method further comprises determining on at least one of these semiconductor regions the as-implanted concentration. The method further comprises partially activating the at least two semiconductor regions. The method further comprises measuring by a photomodulated optical reflectance (PMOR) technique on the partially activated semiconductor regions the signed amplitude of the reflected probe signal as a function of junction depth and for at least two laser separation values. The method further comprises measuring by a PMOR technique on the partially activated semiconductor regions the DC probe reflectivity as a function of junction depth. The method further comprises extracting from these measurements the active doping concentration thereby assuming crystal mobility. The method further comprises calculating the inactive doping concentration using the determined total as-implanted concentration and active doping concentration.

In another aspect, a method of determining the inactive doping concentration of a semiconductor region using a photomodulated optical reflectance (PMOR) method is disclosed. The method comprises providing at least two semiconductor regions having substantially the same as-implanted concentration but different known junction depths, wherein the semiconductor regions being not annealed. The method further comprises performing a photomodulated optical reflectance (PMOR) technique on at least one of these semiconductor regions to determine the as-implanted concentration. The method further comprises partially activating the at least two semiconductor regions. The method further comprises performing a PMOR technique on the partially activated semiconductor regions for at least two different laser separation values to measure the signed amplitude of the reflected probe signal as a function of the junction depth and the DC probe reflectivity as a function of the junction depth. The method further comprises determining based on these measurements the active doping concentration. The method further comprises calculating the inactive doping concentration using the determined total as-implanted concentration and the active doping concentration.

In another aspect, a system for determining the inactive doping concentration of a semiconductor region using a photomodulated optical reflectance (PMOR) method is disclosed. The system comprises means for providing a set of at least two semiconductor regions having substantially the same as-implanted concentration but different known junction depth. The system further comprises means for determining on at least one of these semiconductor regions the as-implanted concentration. The system further comprises means for partially activating the at least two semiconductor regions. The system further comprises means for measuring by a photomodulated optical reflectance (PMOR) technique on the partially activated semiconductor regions the signed amplitude of the reflected probe signal as a function of junction depth and for at least two laser separation values. The system further comprises means for measuring by a PMOR technique on the partially activated semiconductor regions the DC probe reflectivity as a function of junction depth. The system further comprises means for extracting from these measurements the active doping concentration thereby assuming crystal mobility. The system further comprises means for calculating the inactive doping concentration using the determined total as-implanted concentration and active doping concentration.

In another aspect, a system for determining the inactive doping concentration of a semiconductor region using a photomodulated optical reflectance (PMOR) method is disclosed. The system comprises a providing module configured to provide a set of at least two semiconductor regions having substantially the same as-implanted concentration but different known junction depth. The system further comprises a determining module configured to determine on at least one of these semiconductor regions the as-implanted concentration. The system further comprises an activating module configured to partially activate the at least two semiconductor regions. The system further comprises a measuring module configured to measure by a photomodulated optical reflectance (PMOR) technique on the partially activated semiconductor regions (a) the signed amplitude of the reflected probe signal as a function of junction depth and for at least two laser separation values, and (b) the DC probe reflectivity as a function of junction depth. The system further comprises an extracting module configured to extract from these measurements the active doping concentration thereby assuming crystal mobility. The system further comprises a calculating module configured to calculate the inactive doping concentration using the determined total as-implanted concentration and active doping concentration.

BRIEF DESCRIPTION OF THE DRAWINGS

FIGS. 5a-b shows experimental (symbols) vs simulated (lines) obtained values of signed amplitude (TP) for sample CVD3 (10e20 cm-2 total SIMS doping).

DETAILED DESCRIPTION OF CERTAIN ILLUSTRATIVE EMBODIMENTS

Certain embodiments solve problems associated with PMOR techniques, in particular when determining the dopant profile and/or physical parameters of a highly doped semiconductor region. With highly doped is meant, a semiconductor region having an integrated concentration of about 1e20 cm$^{-3}$ or higher.

Certain embodiments relate to methods and/or procedures for determining in a non-destructive way the degree of activation and the active doping profile of a partially activated doped semiconductor region. Such a region can be a doped semiconductor layer formed on a high-resistivity substrate.

Certain embodiments relate to methods and/or procedures for determining in a non-destructive way physical properties of a semiconductor region comprising inactive dopants. Such physical properties can be the complex refractive index, thermal diffusivity, the Shockley-Reed-Hall (SRH) recombination lifetime.

Certain embodiments relate to methods and/or procedures to determine the effect and/or efficiency of annealing steps on physical properties such as complex refractive index, the life-time of the doped semiconductor region, thermal diffusivity, carrier lifetime and/or on the activation of a doped semiconductor region.

In this section the schematics of the TP measurement set-up are discussed. For the purpose of teaching, the TP method is used to measure the semiconductor regions, although the disclosure is not limited to this particular PMOR method. Any PMOR method that provides signed amplitudes can be applied to provide the experimental data needed to determine the physical parameters of the sample(s) studied. The wavelength of the PMOR probe laser is preferably selected to be about $\lambda_{probe} \sim 2\pi n\ 0.15$ nm, with $\lambda_{probe}$ being the wavelength of the probe laser and n the refractive index of the semiconductor region under investigation. For TP the modulation frequency of the pump laser is typically in the mega Hertz range, typically at about 1 MHz, resulting in a dynamic excess carrier profile dependent on the total carrier level as the lifetime of the excess carriers is inverse proportional to the total carrier level.

Figure 1:
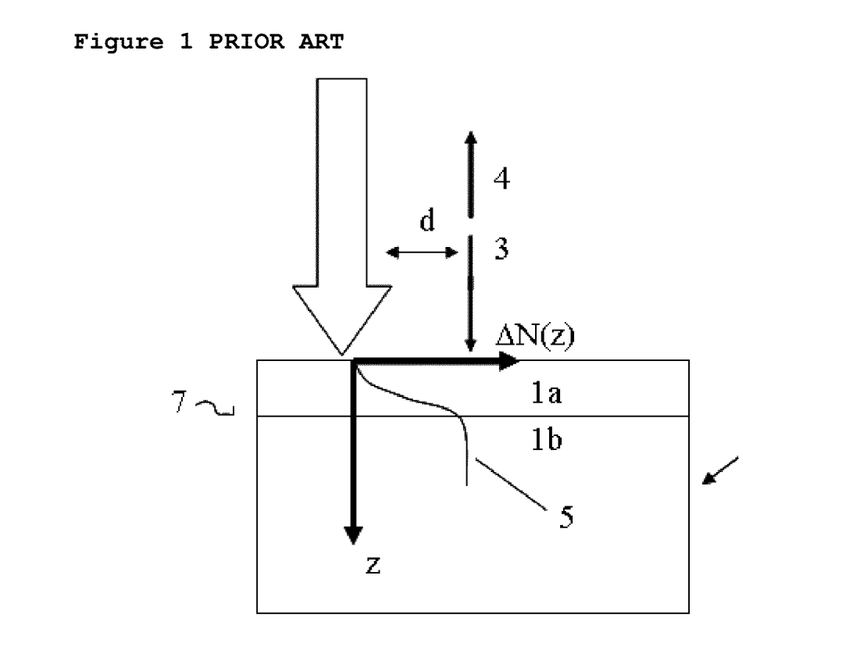
FIG. 1 is an illustration of the conventional Therma Probe (TP) technique applied on a sample.

FIG. 1 shows a sample (7) comprising a semiconductor substrate (1). The semiconductor substrate (1) typically comprises a doped layer (1a) formed on an undoped or lower doped region (1b). The substrate (1) can be formed by depositing an in-situ doped layer (1a) on top of layer (1b), yielding a uniform doping profile over region (1a), also known as box-profile or can be formed by implanting dopants into the substrate (1), yielding a doped region (1a) and an undoped region (1b). By using e.g. ion implantation for implanting dopants into the substrate (1), any kind of doping profile can be obtained depending on the choice of implant species, the energy and implantation dose used. Layer 1a can be doped with a dopant of the same or the opposite type of dopant used to dope the underlying layer 1b.

In FIG. 1, the excess carrier profile $\Delta N(z)$ as function of depth z into the substrate (1) is also shown, indicated by graph 5. A pump laser beam (6) and a probe laser beam (3) impinge from the surroundings (2) on the semiconductor substrate (1). The incident probe laser beam (3) and the reflected probe laser signal (4) are indicated by respectively arrows (3) and (4). The probe laser beam (arrow 3) will be reflected, thus generating the reflected probe laser signal (arrow 4) at various positions on the semiconductor substrate (1).

For example, the probe laser beam (3) may be reflected at the surface, yielding a surface component in the reflected probe laser signal (4). It may also be reflected by a change in the excess carrier profile which can occur at the surface, yielding a near-surface component, or at the interface between the doped part (1a) and undoped part (1b) on the gradient of N(z), yielding a bulk (or interface) component. The probe laser beam may also be reflected at any transition in the doping profile.

Laser beams from both lasers, pump laser (6) and probe laser (3), are superimposed onto each other and may contact the semiconductor substrate (1) in the same or in a different area. Typically, both lasers are in a fixed measurement set-up and both incident laser beams have a direction perpendicular to the wafer surface or substrate surface, meaning incident at a zero angle relative to the wafer surface normal. The spacing (d) between the probe laser (3) and the pump laser (6) can be varied as illustrated in FIG. 1. The power of the probe signal (3) and the time during which each of the measurements is performed are typically kept constant. A large offset d corresponds to almost no excess carriers and therefore little or no signal. A small or zero offset, i.e. both laser beams (3, 6) impinge on substantially the same spot on the semiconductor substrate (1), corresponds to a maximum number of excess carriers and therefore a high signal. When the fixed pump laser power is high enough, one can vary the internal excess carrier level and therefore the origin of the interface component by increasing the beam offset d.

PMOR Modeling on Box-Like Doping Profiles

In this section, a summary of the prior art model for 100% active box-like doping profiles is given and the simulated results are compared with experimental data obtained on Boron (B)-doped chemical vapor deposited (CVD) layers. From this comparison one can conclude that the prior art PMOR extraction techniques fails, in particular for extraction the dopant profile in case high totally integrated doses is present in the semiconductor region under study.

In the past, attempts have been made to model PMOR signals on B-doped CVD layers (1a) using a basic model consisting of three steps. Such a model is disclosed by Bogdanowicz et al. in Journal of Vacuum Science &Technology B, 2008, no 26, p 310-316, and by Dortu et al. in Journal of Vacuum Science & Technology B, 2006, no 24, p 1131-1138, both hereby incorporated by reference in their entirety.

In summary, in a first and most challenging step (transport model), the excess carriers ($\Delta N$) and excess temperature ($\Delta T$) are calculated from the laser characteristics (power, radius, temporal behavior) and sample characteristics (doping profile $N(z)$). This is done by solving respectively the drift-diffusion equations, coupled with additional models to account for variations with doping and excess carrier concentrations in mobility and in Schockly-Reed-Hall (SRH) and Auger recombination rate as well as bandgap narrowing (BGN) to obtain the excess carrier distribution, and solving the heat diffusion equation to obtain the excess temperature distribution.

In a second step, based on the thus obtained excess carriers and excess temperature distributions, the excess refractive index distribution $\Delta n$ is calculated. One of the particularities of this step is that it expects negligible variations in the extinction coefficient k, being the imaginary part of the complex refractive index, but only a change in the real part of the refractive index n.

Finally, the normalized modulated reflectance $\Delta R/R$ is the result of the interference of the reflections at all depths where the excess refractive index changes, i.e. in the case of a box-like profile with junction depth $X_j$, it can be written as.

$$\frac{\Delta R}{R} = -\frac{4}{n_{Si}^2 - 1}\left[\Delta n(z=0) + \cos\left(\frac{4\pi n_0 X_j}{\lambda_{probe}}\right)(\Delta n(z=X_j) - \Delta n(z=0))\right] \quad (1)$$

where $n_0$ is the silicon lattice refractive index i.e. without any free carriers.

Given the finite radius of the probe laser, this equation should actually be integrated over the lateral distribution of the probe power but this has been omitted for the sake of readability.

On a box-like doping profile, the signal is therefore only due to the interference of a surface component (i.e. $\Delta n(z=0)$ due to both excess carriers and temperature) and an interface component (i.e. $\Delta n(z=X_j)$ due to excess carriers only given the almost flat temperature distribution at the scale of wavelength of the probe laser $\lambda_{probe}$).

The signal $\Delta R/R$ can then be split into its contributions respectively in phase and in quadrature with the pump power, which, up to a normalization factor and a constant phase factor, give rise to two independent signals, respectively called I and Q. In this disclosure, however, only the so-called signed amplitude is discussed, i.e. the signal amplitude defined with sign opposite to I.

Figure 2:
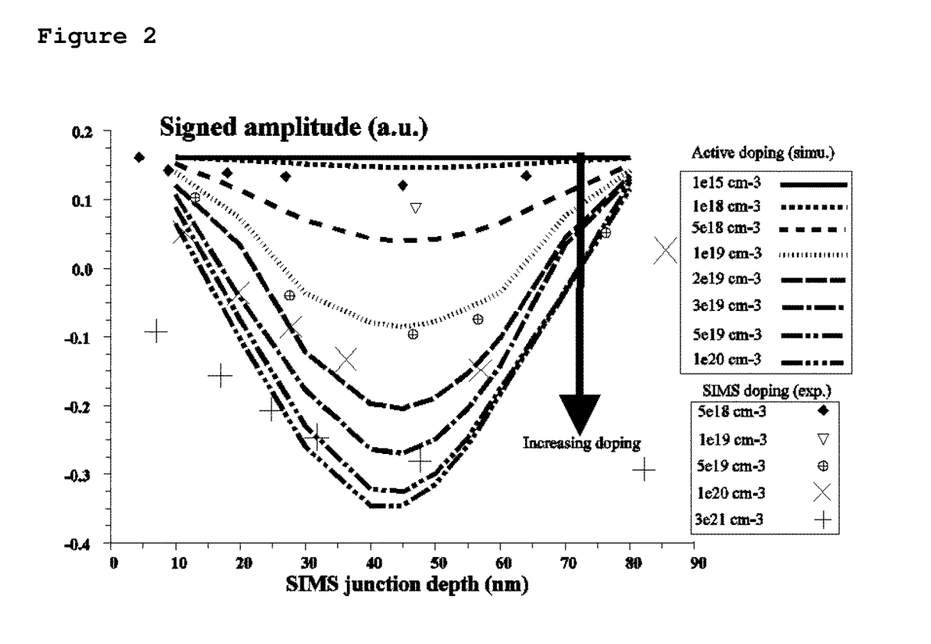
FIG. 2 shows experimental (symbols) vs simulated (lines) obtained values of signed amplitude (TP) as a function of SIMS junction depth with varying doping concentration (total SIMS doping for experimental data and active doping for simulations) when using prior art modeling.

Compared to Bogdanowicz et al in Journal of Vacuum Science & Technology B, 2008, no 26, p 310-316 referenced above where the simulated signed amplitude on homogeneous substrates and box-like CVD layers showed non acceptable discrepancies with the experimental data, it has been found that by taking into account the BGN-induced quasi-electric fields in the transport model, a great improvement is achieved both for substrates (not shown) and box-shaped CVD layers as shown in FIG. 2.

More information about the measured samples is given in Table I of the Bogdanowicz reference above. In spite of the time independence of the simulations, although little time dependence is expected, the signed amplitude obtained in the simulations is now in good qualitative agreement with the experimental data when the measured SIMS doping is below $10^{20}$ cm$^{-3}$. To reach quantitative agreement, lowered (resp. enhanced) activation must be assumed compared to FPP measurements, for SIMS active doping concentrations above (resp. below) $10^{19}$ cm$^{-3}$ as shown in table 1, which provides a summary of the results when analyzing 5 different samples according to embodiments of the disclosure.

TABLE 1

|  | SIMS Total doping (cm-3) | FFP + SIMS average inactive doping (cm$^{-3}$) | FFP + SIMS average active doping (cm$^{-3}$) | TP average active doping (cm$^{-3}$) | TP average $\tau_{SRH}$ (s) | TP average probe $\alpha$ (cm$^{-1}$) | TP average $D_{th}$ (cm$^2$s$^{-1}$) |
|---|---|---|---|---|---|---|---|
| CVD5 | 5 10$^{18}$ | 4.3 10$^{18}$ | 7 10$^{17}$ | 1-2 10$^{18}$ | N/A | N/A | N/A |
| CVD6 | 10$^{19}$ | N/A | N/A | 3-4 10$^{18}$ | N/A | N/A | N/A |
| CVD2 | 5 10$^{19}$ | 3.4 10$^{19\ ii}$ | 1.6 10$^{19}$ | 1-2 10$^{19}$ | N/A | N/A | N/A |
| CVD3 | 10$^{20}$ | 5 10$^{19}$ | 5 10$^{19}$ | 10$^{19}$ | 10$^{-10}$ | 4500 | 0.025 |
| CVD4 | 3 10$^{21}$ | 2.97 10$^{21}$ | 3 10$^{19}$ | 0.5-1 10$^{19}$ | 10$^{-10}$-10$^{-11}$ | 10000 | 0.23 |

The simulated behavior is actually quite simple to understand if four important observations are made. First, the simulated excess temperature is totally independent from the layer characteristics. It appears therefore just as a negative vertical shift in the signed amplitude in Table 1.

Second, the substrate (1b) excess carrier concentration is also independent from the layer characteristics. These two remarks explain why all the simulated cosines reach the same value when $X_j\sim 0$, this value being actually just the signal value obtained on a lowly doped substrate.

Third, the layer excess carrier concentration $\Delta N_l$ is independent from the junction depth $X_j$ and changes with the layer doping concentration N and substrate injection level $\Delta N_{sub}$ as $$\Delta N_l = \frac{1}{N} \frac{N_c^l}{N_c^{sub}} \frac{N_v^l}{N_v^{sub}} \exp\left(\frac{E_g^l - E_g^{sub}}{kT}\right) \Delta N_{sub}^2 \quad (2)$$

where $N_c^l$ (resp. $N_c^{sub}$) and $N_v^l$ (resp. $N_v^{sub}$) are respectively the effective densities of states of the conduction and valence bands in the layer (1) (resp. in the substrate (1b)), $E_g^l$ (resp. $E_g^{sub}$) is the bandgap energy in the layer (1a) (resp. in the substrate (1b)) and kT is the thermal energy (~0.025 eV at T=300K). The increasing amplitude of the cosines with layer doping concentration in FIG. 2 is therefore explained by a decreasing excess carrier concentration in the layer (1a). Notice that equation 2 is derived assuming flat quasi-Fermi levels. This assumption is quantitatively acceptable if not too many carrier recombination and/or generation occur in the layer (1a), i.e. if the layer doping is not too high ($N<10^{20}$ cm$^{-3}$ in our simulations).

Fourth and final observation, the minimum of the cosine at 44 nm ($=\lambda_{probe}/(4n_{Si})$) is the consequence of the destructive interference between the interface and the surface reflections.

For SIMS doping concentrations lower than $10^{20}$ cm$^{-3}$, the behavior is therefore easily understood. For higher doping concentration, however, the simulations are not able to predict even qualitatively the experimental data. While, theoretically, the simulations always predict a cosine behavior for the signed amplitude, the experimental data increasingly deviate from this behavior as the doping concentration rises (mainly x and + symbols of FIG. 2). Furthermore, it seems that the signal behavior with decreasing junction depth no longer converges towards its expected substrate value when $X_j$~0. As disclosed in the next section that this behavior for higher doped samples can be explained if the impact of inactive dopants is considered.

Impact of Inactive Dopants

In this section, it is shown that the qualitative disagreement between experimental and simulated data on highly doped CVD layers as shown in the previous section can be accounted for if the impact of inactive dopants is taken into account. Two sets of the samples with the least cosine-like behavior in FIG. 1 are here discussed; those with respectively $N_{SIMS}$~$10^{20}$ cm$^{-3}$ (CVD3, x of Table 1) and $N_{SIMS}$~3 $10^{21}$ cm$^{-3}$ (CVD4, + of Table 1).

A comparison of the SIMS and FPP results highlighting the partial inactivation of these CVD layers is first shown. A set of samples (7) containing semiconductor regions having substantially the same implanted dose $N_{tot}$, but different junction depth $X_j$. Then, based on a mixed model between 100% active layers (as shown above in the section PMOR modeling on box-lie doping profiles) and amorphous layers, an enhanced model for the PMOR signal on box-like profiles is proposed. Finally, based on DC probe reflectance measurements, the effect of inactive dopants on the optical constants of the doped layer is confirmed.

The comparison of FPP sheet resistance and SIMS measurements on the CVD3 and CVD4 samples shows a respective degradation of the layer conductivity by about a factor 2 and a factor 100, corresponding respectively to 50% and 1% activation of the dopant atoms in these layers if crystalline mobility in the semiconductor region is assumed. It can be deduced that up to 2.7 $10^{21}$ cm$^{-3}$ dopant atoms (for the CVD4 samples) are not in substitutional sites in the lattice (e.g. interstitials, clusters, . . . ) of the semiconductor region and that they therefore perturb the lattice periodicity. As a consequence, there must be a modification in the optical constants (n,k) of the layer and therefore of the absorption coefficient $\alpha$ ($=4\pi k/\lambda_{probe}$), as well as of the relevant transport parameters in the layer (Shockley-Reed-Hall lifetime $\tau_{SRH}$, carrier mobility $\mu$ and thermal diffusivity $D_{th}$).

This situation, albeit milder, can be compared with that of amorphous layers, where these parameters are also modified. Yet, on amorphous layers, the thermally dominated PMOR signals prove to vary linearly with the junction depth. Taking additionally into account the fact that the PMOR behavior for a 100% active doping layer is cosinusoidal as expressed in equation (1), according to an embodiment of disclosure the two behaviors, i.e. crystalline and amorphous, are mixed to account for the signal on partially active layers, i.e.

$$\frac{\Delta R}{R} = A_0 + A_1 \cos\left(\frac{4\pi n_0(X_j + \Delta X_j)}{\lambda_{probe}}\right) - A_2 X_j \quad (3)$$

where $A_0$ and $A_1$ are the typical signals measured on purely active doping profiles, i.e. 100% activation of the dopants in the semiconductor region, and $A_2$ is a signal comparable to the thermal signals measured on amorphous layers. $\Delta X_j$ is an additional parameter to account for variations in the probed junction depth when the lasers are separated as discussed by Bogdanowicz et al in Journal of Vacuum Science &Technology B, 2008, no 26, p 310-316 referenced above.

Figure 3A:
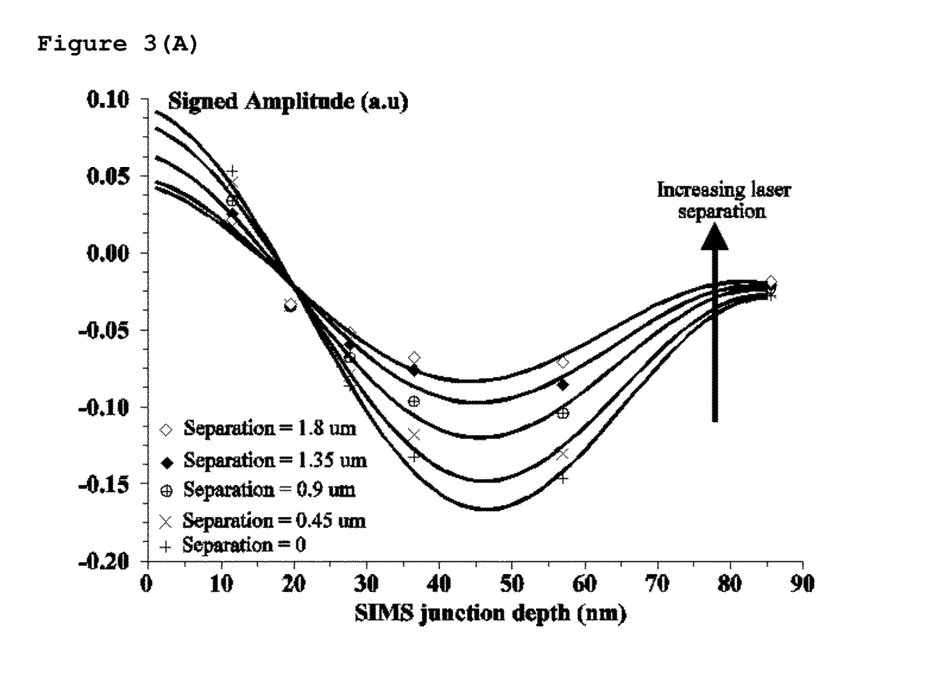
FIGS. 3a-b shows experimental (symbols) vs simulated (lines) obtained values of signed amplitude (TP) as function of SIMS junction depth with varying separation d between the laser beam and the probe beam for two samples given in table 1 (CVD3: 2a, CVD4; 2b) according to an embodiment.
Figure 3B:
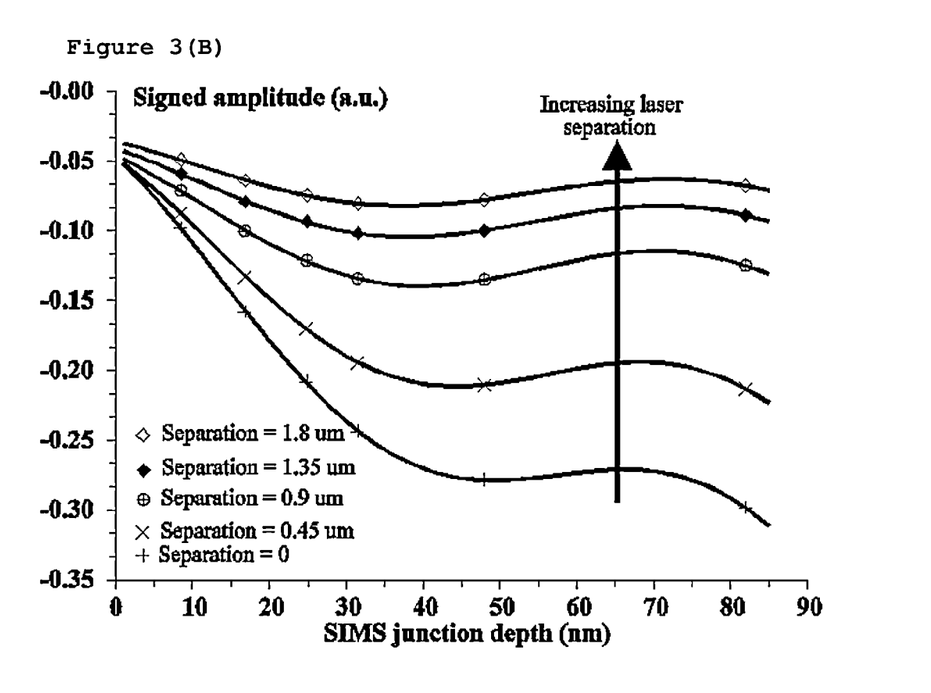

The experimental data on CVD3 and CVD4 can then be fitted with equation (3) for at least two different lateral separations d of the probe and pump lasers as shown in FIGS. 3a and 3b. The fittings are of high quality showing a good match between experimental data and simulation data, which confirms this mixed model. Besides, from these fittings, quantitative physical information can be deduced. The signal contribution $A_2$ is assumed to be purely thermal and its lateral decay is therefore a measure of the thermal diffusion length in the layer, i.e. of the thermal diffusivity $D_{th}$. The obtained $D_{th}$ values with this fitting as listed in table 1 are acceptable, i.e. lower than the crystalline silicon values and higher than the amorphous silicon values as shown by Vitkin I. et al in Journal of Applied Physics, 1990, 67, 2822-30.

Figure 4:
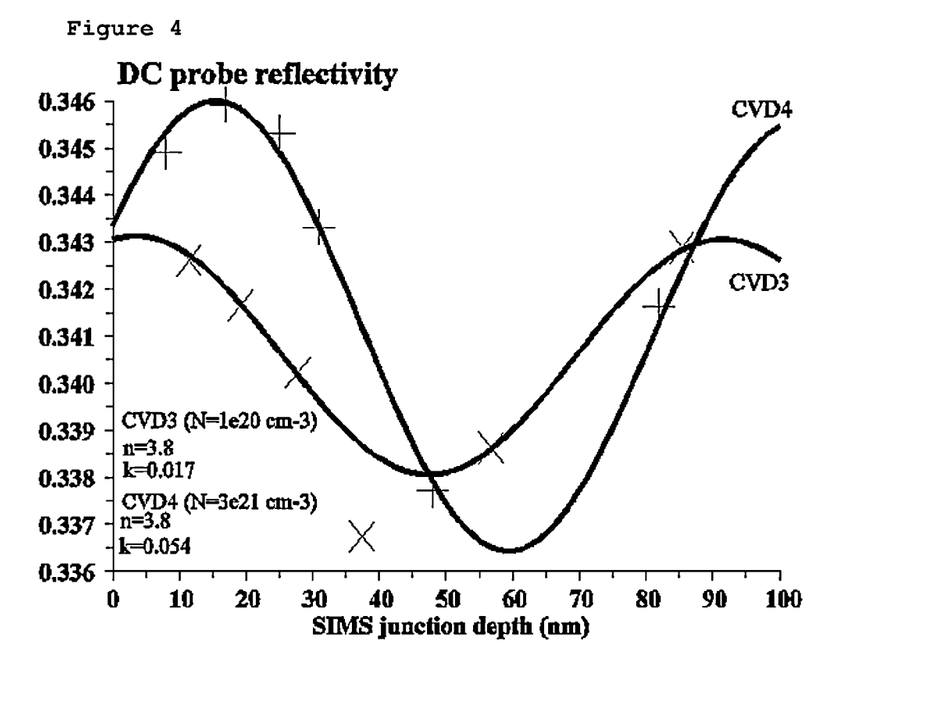
FIG. 4 shows experimental (symbols) vs fitted (lines) obtained values of DC probe reflectance (TP) as function of SIMS junction depth (CVD3: +, CVD4; X) according to an embodiment.

Furthermore, the impact of the partial inactivation of the layer on the optical constants (n,k) can be observed on the measurements of the probe (and also pump) DC reflectance. When fitting the data for CVD3 (+) and CVD4 (X) separately with a multireflection formula taking into account the reflections of the incoming probe laser on the surface of the semiconductor sample, as well as the internal reflections of the transmitted probe laser in the semiconductor sample, it is possible to deduce their respective layer optical constants as shown in FIG. 4. For sample CVD3 having a SIMS total doping of 1e20 cm-3 the multireflection fitting resulted in a real part, refractive index n=3.8 and an imaginary part, extinction coefficient k=0.017. For sample CVD4 having a SIMS total doping of 3e21 cm-3 the multireflection fitting resulted in real refractive index n=3.8 and an extinction coefficient k=0.054.

The relationship between the absorption coefficient cc and the extinction coefficient k is given by $\alpha=(4\pi/\lambda)$ k with $\lambda$ being the wavelength of the light being absorbed. The obtained values indeed show that the known Drude model, accounting for the refractive index change with free carrier concentration, cannot explain the observed behavior as the extinction coefficient would not vary. Namely, quite remarkably, while no change in the extinction coefficient is expected, a modification of up to 500% is observed (see sample CVD4).

If this cannot be explained by the active dopants, this can only be due to inactive dopants. Notice that the obtained values listed in Table 1 are in an acceptable range, i.e. in-between the values of crystalline Si and of amorphous Si. The absorption coefficient for the probe laser $\alpha_{probe}$ is typically about 2001 cm$^{-1}$ in crystalline Si and about 14000 cm$^{-1}$ in amorphous Si. The thermal diffusivity $D_{th}$ is typically 0.45 cm$^2$s$^{-1}$ in crystalline Si and about 0.03 cm$^2$s$^{-1}$ in amorphous Si.

Numerical Simulations

In the previous section, it has qualitatively been shown, based on experimental data, that the impact of inactive dopants can qualitatively explain the observed PMOR behavior of the measured CVD layers. Besides, the actual values of the absorption coefficient and thermal diffusivity of the considered samples have been derived. These values are used in this section as inputs for numerical simulations to show that the signal behavior on CVD3 and CVD4 samples can also be quantitatively understood.

There, however, remain two unknowns, namely the modified mobility µ and SRH lifetime $\tau_{SRH}$ in the layer. Given the insensitivity of the PMOR signal to layer mobility as shown in Equation 2, crystalline Si mobility will be assumed for the highly dopes samples while $\tau_{SRH}$ will be used as a fitting parameter. In the case of CVD3, the experimental signed amplitude is well reproduced if the active doping concentration of the layer is $10^{19}$ cm$^{-3}$ and $\tau_{SRH}$ is $10^{-10}$ s (FIG. 5a), which means 10% activation (50% according to FPP) and a $\tau_{SRH}$ degradation factor of about 100 compared to a fully activated layer with the same SIMS doping concentration. The change in $\tau_{SRH}$ seems to be what dominates the signal even though the increase in absorption coefficient also tends to have an effect for the deepest junctions (FIG. 5b). Note that the lack of agreement on the deepest sample can notably be accounted for by its better activation. Further, the lateral behavior (impact of laser separation) is simulated with an acceptable error even though the decay length is overestimated (FIG. 5b). The results of this study and of the simulations are summarized in Table 1.

Finally, the experimental data presented for CVD4 can be reproduced considering an active doping in the range $0.5\ 10^{19}$ to $10^{19}$ cm$^{-3}$ (0.2 to 0.6% activation vs. 1% according to FPP) and $\tau_{SRH}$ in the range between $10^{-10}$ s and $10^{-11}$ s (degradation factor ~10). However, the signal sensitivity in these active doping and SRH lifetime ranges is such that one unique value of these parameters cannot be found to account simultaneously for the data on all the layers (not shown).

As a final remark, it is to be noted that active and inactive dopants have a very different impact on both the temperature and plasma contributions to the signal.

First, while the active dopants do not influence the temperature contribution, the latter always increases linearly with $X_j$ when some inactive dopants are present.

Second, according to the simulations, the junction potential ($V_1 - V_{sub}$) is almost independent from the inactive dopant concentration. Yet, the ratio of carrier injection $\Delta N_{sub}/\Delta N_1$ is directly related to the junction potential via (if flat Fermi levels are assumed)

$$-q(V_l - V_{sub}) = kT\ln\left(\frac{\Delta N_{sub} N_c^l}{\Delta N_l N_c^{sub}}\right) + (\Delta E_{g,c}^{sub} - \Delta E_{g,c}^l) \quad (4)$$

where q is the electron charge and $\Delta E^{sub}_{g,c}$ and $\Delta E^{l}_{g,c}$ are the reductions in conduction band energies respectively in the substrate (1b) and in the layer (1a). This ratio is therefore almost activation independent (if Boltzmann statistics is assumed and BGN is neglected). By factorizing out the plasma component of the signal Equation (1), one obtains $$\Delta N_{sub}\underbrace{\left(\frac{\Delta N_l}{\Delta N_{sub}} + \left(1 - \frac{\Delta N_l}{\Delta N_{sub}}\right)\cos\left(\frac{4\pi n_0 X_j}{\lambda_{probe}}\right)\right)}_{activation\text{-}independent} \quad (5)$$

it can be deduced that the active and inactive parts of the layer doping do not impact the plasma signal in the same way. The active doping concentration determines the junction potential and therefore the injection ratio, which fixes most of the signal behavior (activation independent part of Equation. (5)). The inactive doping reduces the substrate injection, and the layer injection to keep their ratio constant, and acts therefore essentially to minimize the variations in plasma signal. In total, the inactive dopants enhance the temperature signal and lower the plasma signal.

Extraction Procedure

In the previous sections the deficiencies of the prior art PMOR methods are discussed as they assume 100% activation of the sample under study after anneal, while the impact of inactive dopants on the optical properties and signals of the PMOR method was disclosed. In this section, the previous sections are used to establish a procedure for determining the dopant profile and/or physical parameters of a highly doped semiconductor region. With highly doped is meant, a semiconductor region having an integrated concentration of about 1e20 cm$^{-3}$ or higher.

This procedure allows determining in a non-destructive way the degree of activation and the active doping profile of a partially activated doped semiconductor region. Such a region can be a doped semiconductor layer formed on a high-resistivity substrate.

This procedure allows determining in a non-destructive way physical properties of a semiconductor region comprising inactive dopants. Such physical properties can be the complex refractive index, the life-time of the doped semiconductor region. For lower concentration levels also a partial activation can be obtained depending on e.g. the thermal budget used to activate these dopants. Indicative for the partial activation of a doped semiconductor layer or semiconductor region is the unexpected behavior of the PMOR signal.

This unexpected behavior is noticed by the non-cosine behavior of the signal amplitude as function of the junction depth. This can be seen in FIG. 2 where for a sample with experimental SIMS concentration of 3e21 cm$^{-3}$ (CVD4) the + symbols don't follow the same cosine behavior as the other samples. In case of a TP signal typically a small negative signed amplitude value is to be expected due to the excess carriers. If however a strongly negative signed amplitude value is obtained, this is an indication that inactive dopants are present in the sample, modifying the physical properties thereof.

As discussed in the previous sections the unknown parameters of a doped semiconductor region (7) under study are the doping profile of the active dopants $N_{act}$ and the doping profile of the inactive dopants $N_{inact}$. While determining the inactive dopant profile $N_{inact}$, one can also determine the modified SRH lifetime $\tau_{SRH}$, the modified absorption coefficient α, the modified thermal diffusivity $D_{th}$ and the modified mobility µ. Also the real and imaginary part of the reflection coefficient (n,k) can be determined.

In order to determine these parameter(s), one needs a set of semiconductor samples (7). These semiconductor regions have substantially the same total implanted dopant concentration $N_{tot}$ while the junction depth $X_j$ although known, may vary from one sample to another. These samples are not annealed. These semiconductor regions (1a) can be formed on the same substrate (1), e.g. by performing different ion implantations in different regions (1a) of the substrate (1). These semiconductor regions (1a) can be formed on different substrates (1).

In a first process this total doping concentration $N_{tot}$ is determined by performing a PMOR measurement, e.g. a TP measurement, on at least one of the samples. A. Salnick et al discloses in "*Quantitative photothermal characterization of ion-implanted layer in Si*" in Journal of Applied Physics, vol 91, no 5 p 2874 to 2882 the application of the TP method for determining the total doping concentration of a doped semiconductor region. As the semiconductor region is inactivated the PMOR signal will essentially by composed of the thermal-wave component as negligible amounts of excess carriers are generated. This publication is hereby incorporated by reference. From this measurement the implanted concentration ($1/cm^3$) can be determined, and, as the junction depth is known for the measured sample, the implanted dose ($1/cm^2$) can be calculated.

After determining the total concentration $N_{tot}$ of the inactive samples, these samples are partially activated, e.g. by thermal annealed. During annealing the dopants will be at least partially activated depending on the thermal budget provided during this anneal process. The purpose of this process is to obtain a partial activation of the doped semiconductor region.

As discussed above, given the little sensitivity of the PMOR signal to the layer mobility (Equation 2) as expressed by the absence of the mobility in this equation, the modified mobility $\mu$ is assumed to be substantially equal to crystalline Si mobility for the highly doped samples.

From measured data, such as shown in FIG. 3a whereby the signed amplitude of the PMOR signal is obtained on at least two different samples with different junction depths, one can determine using equation 3 above the modified thermal diffusivity $D_{th}$. For the samples shown in FIG. 3a the modified thermal diffusivity $D_{th}$ was found to be 0.025 $cm^2 s^{-1}$.

Knowing the modified mobility $\mu$ or assuming a physical meaningful value and after having determined the modified thermal diffusivity $D_{th}$ one can determine using experimental data such as shown in FIG. 4 the modified absorption coefficient cc and the refraction index (n,k). The absorption coefficient for the samples shown in FIG. 4 was found to be about 4500 $cm^{-1}$.

Figure 5A:
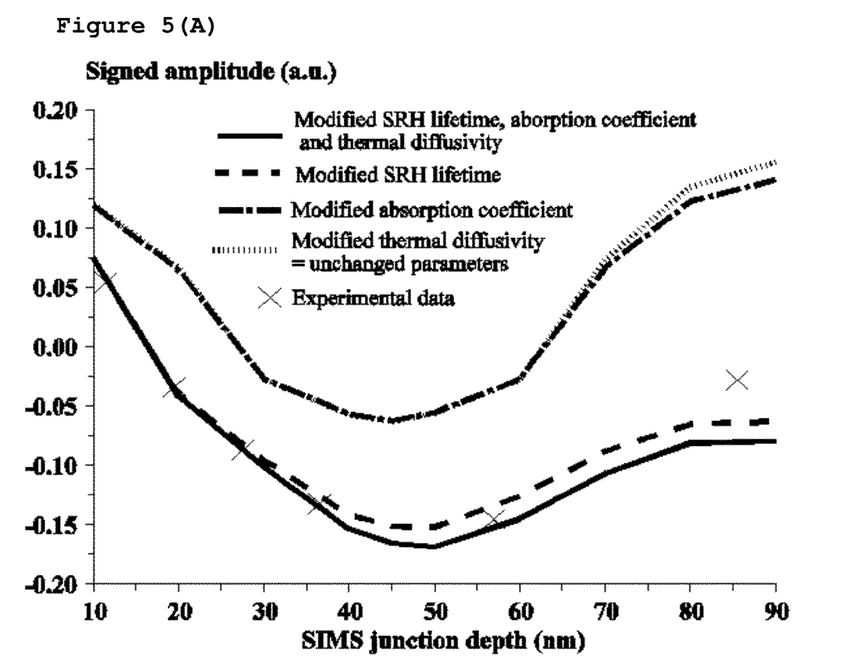
FIG. 5a shows the impact of different simulation parameters on the simulated signed amplitude whereby probe laser and pump laser are not separated (d=0).
Figure 5B:
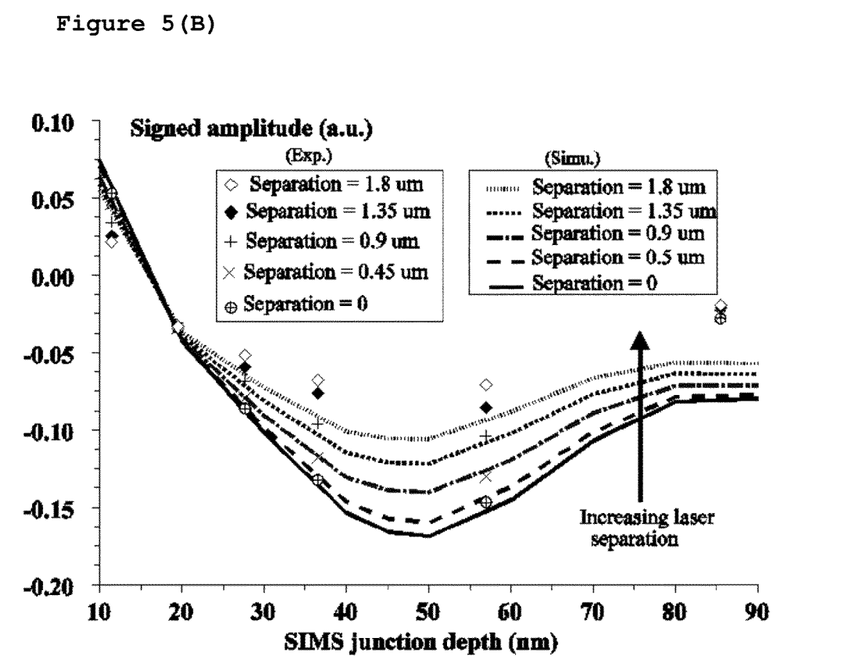
FIG. 5b shows the impact of the separation d between probe laser and pump laser on the simulated signed amplitude according to an embodiment.

Knowing the modified mobility $\mu$ or assuming a physical meaningful value, and after determining the modified thermal diffusivity $D_{th}$ and the modified absorption coefficient $\alpha$ one can determine using experimental data such as shown in FIG. 5a the modified SRH lifetime $\tau_{SRH}$ and the active doping concentration $N_{act}$.

As the total inactive doping concentration $N_{tot}$ was determined in a first process, the inactive doping concentration $N_{inact}$ and the degree of activation can be determined from $N_{tot}$ and $N_{act}$.

Figure 6:
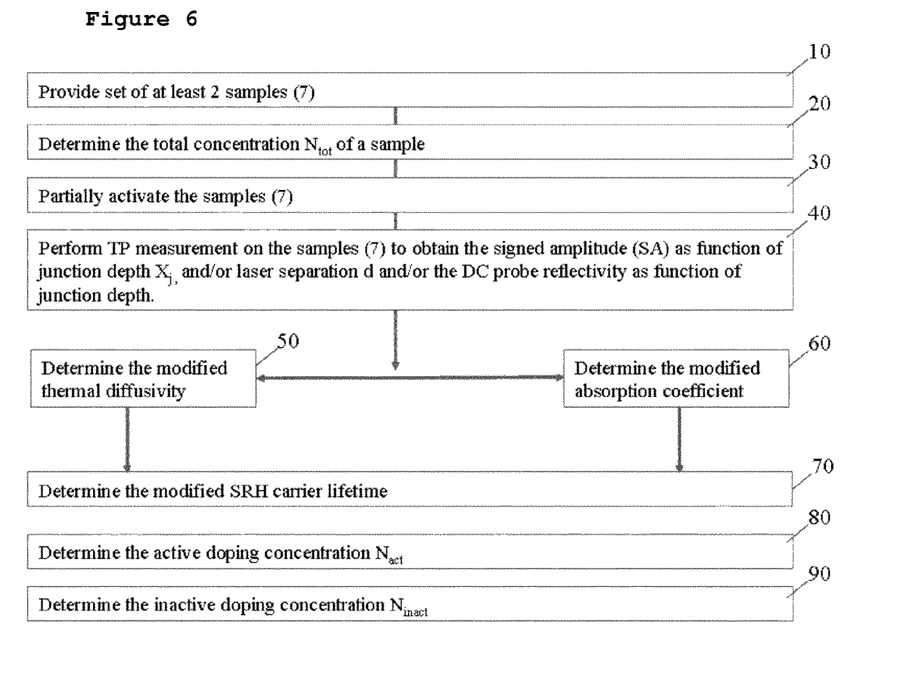
FIG. 6 is a flowchart illustrating an extraction procedure according to an embodiment of the disclosure.

The flowchart given in FIG. 6 illustrates the extraction procedure.

First a set of samples (2) is provided (10). A sample (7) contains a semiconductor region (1a) with a total inactive implanted concentration $N_{toti}$ and a junction depth $X_{ji}$ with i being an integer corresponding to the number of samples in the set. Each sample has substantially the same implanted concentration $N_{toti}=N_{toti+1}=N_{tot}$, while the junction depth differs from one sample to another $X_{ji}<>X_{ji+1}$, whereby each of these junction depths is known. One of the samples (7) of this set of samples a PMOR measurement is performed to determine the common total inactive implanted concentration $N_{tot}$. As the implanted samples are not activated essentially no contribution from excess carriers is present in the PMOR signal (20).

Then the set of samples is partially activated e.g. by annealing.

On the set of samples PMOR measurements are performed to obtain the signed amplitude (SA) and the DC probe reflectivity as function of junction depth $X_j$. (40), and/or as function of laser separation d. One can perform separate measurements to obtain the signed amplitude and DC probe reflectivity or obtain these values during the same measurement.

From the signed amplitude as function of junction depth and using equation (3) for at least two different laser separations d, one can determine the modified thermal diffusivity $D_{th}$, the modified mobility $\mu$ being assumed to be substantially equal to crystalline Si mobility for the highly doped samples (50).

One can determine (60) the refraction index (n,k) and the modified absorption coefficient by fitting the DC probe reflectivity as function of junction depth $X_j$. Determining the absorption coefficient can be done in parallel with determining the thermal diffusivity (50) or thereafter.

Knowing the mobility by assuming a physical meaningful value such as the mobility of crystalline silicon, the thermal diffusivity (50), the absorption coefficient (60) one can determine the lifetime $\tau_{SRH}$ and the active doping concentration $N_{act}$ by fitting (70) the signed amplitude as function of the junction depth $X_j$.

Finally one can determine (80) the inactive doping concentration $N_{inact}$ and degree of activation $N_{act}/N_{tot}$ can be determined (90) as $N_{tot}$ and $N_{act}$ are now known.

In case of box-like doping profiles, one can assume the profile of active and inactive dopants to be constant over the thickness of the doped semiconductor region (1a). This way the presented method provides an active and inactive doping concentration as the junction depth is known.

The foregoing description details certain embodiments of the invention. It will be appreciated, however, that no matter how detailed the foregoing appears in text, the invention may be practiced in many ways. It should be noted that the use of particular terminology when describing certain features or aspects of the invention should not be taken to imply that the terminology is being re-defined herein to be restricted to including any specific characteristics of the features or aspects of the invention with which that terminology is associated.

While the above detailed description has shown, described, and pointed out novel features of the invention as applied to various embodiments, it will be understood that various omissions, substitutions, and changes in the form and details of the device or process illustrated may be made by those skilled in the technology without departing from the spirit of the invention. The scope of the invention is indicated by the appended claims rather than by the foregoing description. All changes which come within the meaning and range of equivalency of the claims are to be embraced within their scope.

What is claimed is:

1. A method of determining the inactive doping concentration of a semiconductor region using a photomodulated optical reflectance (PMOR) method, the method comprising:
   providing a set of at least two semiconductor regions having substantially the same known as-implanted concentration but known varying junction depth;
   determining on at least one of these semiconductor regions the as-implanted concentration;
   partially activating the at least two semiconductor regions;
   measuring by a photomodulated optical reflectance (PMOR) technique on the partially activated semiconductor regions the signed amplitude of a reflected probe signal as a function of junction depth, the PMOR technique comprising applying a pump laser beam and a probe laser beam to the semiconductor regions, the pump laser beam being separated from the probe laser beam by a distance, wherein the measuring of the signed amplitude of the reflected probe signal is performed for two different values of the distance between the pump laser beam and the probe laser beam;

measuring by the PMOR technique on the partially activated semiconductor regions the DC probe reflectivity as a function of junction depth;

extracting from these measurements the active doping concentration thereby assuming crystal mobility;

extracting from these measurements thermal diffusivity, refraction index, absorption coefficient, and/or Shockley-Reed-Hall lifetime; and calculating the inactive doping concentration using the determined total as-implanted concentration and active doping concentration.

2. The method according to claim 1, wherein the PMOR technique is a high-modulation-frequency PMOR technique providing a signal in-phase with modulation signal and a signal with a 90° phase difference with respect to the probe laser beam.

3. The method according to claim 2, wherein the modulation frequency of the pump laser beam is in the Mhz range.

4. The method according to claim 1, wherein the semiconductor regions have an integrated concentration of about 1e20 cm$^{-3}$ or higher.

5. The method according to claim 1, further comprising extracting the junction depth for the partially activated semiconductor regions from the DC probe reflectivity measurements.

6. A method of determining the effect and/or efficiency of an annealing process on physical properties of a doped semiconductor region, the method comprising:

(a) providing at least one sample of the doped semiconductor region;

(b) determining an as-doped doping profile of the at least one sample;

(c) applying an anneal process to the at least one sample; and (d) extracting the selected physical property from the annealed sample according to the method of claim 1.

7. The method according to claim 6, further comprising:

repeating processes (a) to (d) for another sample wherein another anneal process is applied; and correlating the variation in the physical property to the variation in the anneal processes.

8. The method according to claim 6, wherein the physical property is selected from the group of: thermal diffusivity, complex refraction index, absorption coefficient, and/or Shockley-Reed-Hall lifetime.

9. A method of determining the inactive doping concentration of a semiconductor region using a photomodulated optical reflectance (PMOR) method, the method comprising:

providing at least two semiconductor regions having substantially the same as-implanted concentration but different known junction depths, wherein the semiconductor regions being not annealed;

performing a photomodulated optical reflectance (PMOR) technique on at least one of these semiconductor regions to determine the as-implanted concentration;

partially activating the at least two semiconductor regions;

performing a PMOR technique on the partially activated semiconductor regions to measure the signed amplitude of a reflected probe signal as a function of the junction depth and the DC probe reflectivity as a function of the junction depth, the PMOR technique comprising applying a pump laser beam and a probe laser beam to the semiconductor regions, the pump laser beam being separated from the probe laser beam by a distance, wherein the measurement of the signed amplitude of the reflected probe signal is performed for two different values of the distance between the pump laser beam and the probe laser beam;

determining based on these measurements the active doping concentration; and calculating the inactive doping concentration using the determined total as-implanted concentration and the active doping concentration.

10. A system for determining the inactive doping concentration of a semiconductor region using a photomodulated optical reflectance (PMOR) method, the PMOR method comprising:

providing a set of at least two semiconductor regions having substantially the same as-implanted concentration but different known junction depth;

determining on at least one of these semiconductor regions the as-implanted concentration;

partially activating the at least two semiconductor regions;

measuring by a photomodulated optical reflectance (PMOR) technique on the partially activated semiconductor regions the signed amplitude of a reflected probe signal as a function of junction depth, the PMOR technique comprising applying a pump beam and a probe laser beam to the semiconductor regions, the pump laser beam being separated from the probe laser beam by a distance, wherein the measuring of the signed amplitude of the reflected probe signal is performed for two different values of the distance between the pump laser beam and the probe laser beam;

measuring by the PMOR technique on the partially activated semiconductor regions the DC probe reflectivity as a function of junction depth;

extracting from these measurements the active doping concentration thereby assuming crystal mobility; and calculating the inactive doping concentration using the determined total as-implanted concentration and active doping concentration.

11. The system according to claim 10, further comprising extracting the junction depth for the partially activated semiconductor regions from the DC probe reflectivity measurements.

12. A system for determining the inactive doping concentration of a semiconductor region using a photomodulated optical reflectance (PMOR) method, the PMOR method comprising:

providing a set of at least two semiconductor regions having substantially the same as-implanted concentration but different known junction depth;

determining on at least one of these semiconductor regions the as-implanted concentration;

partially activating the at least two semiconductor regions;

measuring by a photomodulated optical reflectance (PMOR) technique on the partially activated semiconductor regions (a) the signed amplitude of a reflected probe signal as a function of junction depth, and (b) the DC probe reflectivity as a function of junction depth, the PMOR technique comprising applying a pump laser beam and a probe laser beam to the semiconductor regions, the pump laser beam being separated from the probe laser beam by a distance, wherein the measurement of the signed amplitude of the reflected probe signal is performed for two different values of the distance between the pump laser beam and the probe laser beam;

extracting from these measurements the active doping concentration thereby assuming crystal mobility; and calculating the inactive doping concentration using the determined total as-implanted concentration and active doping concentration.

13. The system according to claim 12, further comprising extracting thermal diffusivity, refraction index, absorption coefficient, and/or Shockley-Reed-Hall lifetime from these measurements.

14. The system according to claim 12, wherein the semiconductor regions have an integrated concentration of about $1e20\ cm^{-3}$ or higher.

15. The system according to claim 12, wherein the PMOR technique is a high-modulation-frequency PMOR technique providing a signal in-phase with modulation signal and a signal with a 90° phase difference with respect to the probe laser beam.

16. The system according to claim 15, wherein the modulation frequency of the pump laser beam is in the Mhz range.

17. The system according to claim 12, wherein the extracting extracts the junction depth for the partially activated semiconductor regions from the DC probe reflectivity measurements.

* * * * *

UNITED STATES PATENT AND TRADEMARK OFFICE
CERTIFICATE OF CORRECTION

| | |
|---|---|
| PATENT NO. | : 8,817,262 B2 |
| APPLICATION NO. | : 13/689540 |
| DATED | : August 26, 2014 |
| INVENTOR(S) | : Janusz Bogdanowicz |

Page 1 of 1

It is certified that error appears in the above-identified patent and that said Letters Patent is hereby corrected as shown below:

In the Specification:

In column 7 at line 18, Change "-Reed-" to -- -Read- --.

In column 10 at line 38, Change "cm-3" to --$cm^{-3}$--.

In column 10 at line 41, Change "cm-3" to --$cm^{-3}$--.

In column 10 at line 44, Change "cc" to --α--.

In column 13 at line 32, Change "cc" to --α--.

In the Claims:

In column 16 at line 24, In Claim 10, after "pump" insert --laser--.

Signed and Sealed this
Second Day of June, 2015

Michelle K. Lee
*Director of the United States Patent and Trademark Office*